(12) United States Patent
Hashimoto

(10) Patent No.: US 10,156,530 B2
(45) Date of Patent: Dec. 18, 2018

(54) GROUP III NITRIDE WAFERS AND FABRICATION METHOD AND TESTING METHOD

(71) Applicants: SIXPOINT MATERIALS, INC., Buellton, CA (US); SEOUL SEMICONDUCTOR CO., LTD., Danwon-gu, Ansan-si, Gyeonggi-do (KR)

(72) Inventor: Tadao Hashimoto, Santa Barbara, CA (US)

(73) Assignees: SixPoint Materials, Inc., Buellton, CA (US); Seoul Semiconductor Co., Ltd., Ansan-si (KR)

( * ) Notice: Subject to any disclaimer, the term of this patent is extended or adjusted under 35 U.S.C. 154(b) by 440 days.

(21) Appl. No.: 14/806,644

(22) Filed: Jul. 22, 2015

(65) Prior Publication Data
US 2015/0330919 A1    Nov. 19, 2015

Related U.S. Application Data

(62) Division of application No. 13/798,530, filed on Mar. 13, 2013.
(Continued)

(51) Int. Cl.
*G01N 23/207* (2018.01)
*C01B 21/06* (2006.01)
(Continued)

(52) U.S. Cl.
CPC ......... *G01N 23/207* (2013.01); *B24B 37/044* (2013.01); *C01B 21/0632* (2013.01);
(Continued)

(58) Field of Classification Search
None
See application file for complete search history.

(56) References Cited

U.S. PATENT DOCUMENTS 6,656,615 B2    12/2003    Dwiliński et al.
7,078,731 B2    7/2006    D'Eyelyn et al.
(Continued)

FOREIGN PATENT DOCUMENTS

CN    101388427 A    3/2009
CN    101432471 A    5/2009
(Continued)

OTHER PUBLICATIONS

Tonshoff et al (Measurement of Sub Surface Damage in Silicon Wafers, Progress in Precision Engineering, Springer, Berlin, Heidelberg, (1991) pp. 319-320).*

(Continued)

*Primary Examiner* — Melvin C. Mayes
*Assistant Examiner* — Michael Forrest
(74) *Attorney, Agent, or Firm* — Strategic Innovation IP Law Offices, P.C.

(57) ABSTRACT

The invention provides, in one instance, a group III nitride wafer sliced from a group III nitride ingot, polished to remove the surface damage layer and tested with x-ray diffraction. The x-ray incident beam is irradiated at an angle less than 15 degree and diffraction peak intensity is evaluated. The group III nitride wafer passing this test has sufficient surface quality for device fabrication. The invention also provides, in one instance, a method of producing group III nitride wafer by slicing a group III nitride ingot, polishing at least one surface of the wafer, and testing the surface quality with x-ray diffraction having an incident beam angle less than 15 degree to the surface. The invention also provides, in an instance, a test method for testing the
(Continued)

surface quality of group III nitride wafers using x-ray diffraction having an incident beam angle less than 15 degree to the surface.

19 Claims, 2 Drawing Sheets

Related U.S. Application Data

(60) Provisional application No. 61/706,012, filed on Sep. 26, 2012.

(51) Int. Cl.

| | | |
|---|---|---|
| H01L 21/306 | (2006.01) | |
| H01L 21/02 | (2006.01) | |
| H01L 29/04 | (2006.01) | |
| C30B 29/40 | (2006.01) | |
| C30B 33/00 | (2006.01) | |
| C30B 33/06 | (2006.01) | |
| B24B 37/04 | (2012.01) | |
| H01L 21/66 | (2006.01) | |
| H01L 29/20 | (2006.01) | |
| H01L 21/78 | (2006.01) | |
| C30B 7/10 | (2006.01) | |

(52) U.S. Cl.
CPC .......... *C30B 29/403* (2013.01); *C30B 29/406* (2013.01); *C30B 33/00* (2013.01); *C30B 33/06* (2013.01); *H01L 21/0201* (2013.01); *H01L 21/30625* (2013.01); *H01L 21/78* (2013.01); *H01L 22/12* (2013.01); *H01L 29/045* (2013.01); *H01L 29/2003* (2013.01); *C01P 2002/74* (2013.01); *C30B 7/105* (2013.01); *H01L 2924/0002* (2013.01)

(56) References Cited

U.S. PATENT DOCUMENTS

| | | |
|---|---|---|
| 7,132,730 B2 | 11/2006 | Dwiliński et al. |
| 7,160,388 B2 | 1/2007 | Dwiliński et al. |
| 7,872,331 B2 | 1/2011 | Ishibashi et al. |
| 8,147,612 B2 | 4/2012 | Uemura et al. |
| 8,299,490 B2 | 10/2012 | Oya et al. |
| 8,921,231 B2 | 12/2014 | Hashimoto et al. |
| 9,202,872 B2 | 12/2015 | Hashimoto et al. |
| 9,518,340 B2 | 12/2016 | Hashimoto et al. |
| 9,543,393 B2 | 1/2017 | Hashimoto et al. |
| 10,024,809 B2 | 7/2018 | Hashimoto |
| 2002/0185054 A1 | 12/2002 | Xu et al. |
| 2002/0186368 A1 | 12/2002 | Rosengaus et al. |
| 2004/0038544 A1 | 2/2004 | Zhang et al. |
| 2005/0103257 A1 | 5/2005 | Xu et al. |
| 2005/0142391 A1 | 6/2005 | Dmitriev et al. |
| 2005/0286590 A1 | 12/2005 | Lee |
| 2006/0124956 A1 | 6/2006 | Peng |
| 2007/0131214 A1 | 6/2007 | Komeda |
| 2007/0178807 A1 | 8/2007 | Gupta et al. |
| 2007/0234946 A1 | 10/2007 | Hashimoto et al. |
| 2008/0008855 A1 | 1/2008 | D'Evelyn et al. |
| 2008/0182092 A1 | 7/2008 | Bondokov et al. |
| 2009/0236694 A1 | 9/2009 | Mizuhara et al. |
| 2009/0315151 A1 | 12/2009 | Hashimoto et al. |
| 2010/0006082 A1 | 1/2010 | Glinski et al. |
| 2010/0031875 A1 | 2/2010 | D'Evelyn |
| 2010/0044718 A1 | 2/2010 | Hanser et al. |
| 2010/0193664 A1 | 8/2010 | Stoddard |
| 2010/0200955 A1 | 8/2010 | Oshima |
| 2010/0219505 A1 | 9/2010 | D'Evelyn |
| 2010/0270649 A1 | 10/2010 | Ishibashi et al. |
| 2012/0000415 A1 | 1/2012 | D'Evelyn et al. |
| 2014/0061662 A1 | 3/2014 | Hashimoto et al. |
| 2014/0065796 A1 | 3/2014 | Hashimoto et al. |
| 2014/0084297 A1 | 3/2014 | Hashimoto et al. |
| 2014/0087113 A1 | 3/2014 | Hashimoto et al. |
| 2014/0087209 A1 | 3/2014 | Hashimoto et al. |
| 2014/0124826 A1 | 5/2014 | Ishibashi et al. |
| 2015/0329361 A1 | 11/2015 | Hashimoto |
| 2016/0040318 A1 | 2/2016 | Hashimoto et al. |

FOREIGN PATENT DOCUMENTS

| | | |
|---|---|---|
| CN | 100577894 C | 1/2010 |
| CN | 101800170 A | 8/2010 |
| CN | 101884094 A | 11/2010 |
| CN | 102212883 A | 10/2011 |
| EP | 2031103 A1 | 3/2009 |
| JP | 2004530306 A | 9/2004 |
| JP | 2007153712 A | 6/2007 |
| JP | 2007297263 A | 11/2007 |
| JP | 2009044138 A | 2/2009 |
| JP | 2010222247 A | 10/2010 |
| JP | 2011042566 A | 3/2011 |
| JP | 2011100860 A | 5/2011 |
| JP | 2011121803 A | 6/2011 |
| JP | 2011219304 A | 11/2011 |
| JP | 2012031028 A1 | 2/2012 |
| JP | 2013177256 A | 9/2013 |
| TW | I226391 B | 1/2005 |
| TW | 201002879 A | 1/2010 |
| TW | 201002880 A1 | 1/2010 |
| WO | 2004053206 A1 | 6/2004 |
| WO | 2007008198 A1 | 1/2007 |
| WO | 2007117689 A2 | 10/2007 |
| WO | 2008042020 A2 | 4/2008 |
| WO | 2009149300 A1 | 12/2009 |
| WO | 2009151642 A1 | 12/2009 |
| WO | 2010017232 A1 | 2/2010 |
| WO | 2010025153 A1 | 3/2010 |
| WO | 2010088046 A1 | 8/2010 |
| WO | 2014035481 A1 | 3/2014 |
| WO | 2014051684 A1 | 4/2014 |
| WO | 2014051692 A1 | 4/2014 |

OTHER PUBLICATIONS

Novikov et al (Observation of defects in crystal surface layers by grazing-incidence diffraction x-ray topography, J Phys D: Appl. Phys. 28 (1995) A84-A87).*
Aida et al (Chemical Mechanical Polishing of Gallium Nitride with Colloidal Silica, J Elec Soc, 158(12), (2011), pp. H1206-H1212).*
Wang et al (X-Ray Diffraction Observation of Surface Damage in Chemical-Mechanical Polished Gallium Arsenide, J Elect Mat. vol. 21, No. 1, (1992) pp. 23-31).*
U.S. Appl. No. 13/834,871, Notice of Allowance dated Oct. 24, 2016.
JP 2015-533039 Japanese Office Action dated Sep. 16, 2016.
JP 2015-529788 Japanese Office Action dated Sep. 26, 2016.
TW 102130676 Office Action with Search Report dated Nov. 10, 2016.
CN 201380055415.2 Office Action dated Dec. 13, 2016.
TW 102134599 Office Action and Search Report (with English translation) dated Dec. 20, 2016.
JP 2015-533039 Office Action dated Jan. 13, 2017.
Wu Tao, "Researches on the Surface Quality of Sapphire Single Crystal ELID Grinding," Chinese Master's Theses Full-text Database-Engineering Science and Technology I, vol. 2, Aug. 15, 2007.
PCT/US2013/030913 International Search Report and Written Opinion dated Jun. 5, 2013 (9 pgs.).
PCT/US2013/032006 International Search Report and Written Opinion dated Jun. 25, 2013 (14 pgs.).
PCT/US2013/032103 International Search Report and Written Opinion dated Jun. 25, 2013 (17 pgs.).
Aoki, M., et al., "GaN Single Crystal Growth Using High-Purity Na as a Flux," Elsevier, Journal of Crystal Growth, pp. 70-76; 242, Apr. 12, 2002.

(56) References Cited

OTHER PUBLICATIONS

Croce, et al., "Étude Des Couches Minces Et Des Surfaces Par Réflexion Rasante, Spéculaire Ou Diffuse, De Rayons X," Revue De Physique Appliquee, vol. 11, No. 1, pp. 113-125, Jan. 1, 1976, XP1417455; (English translation of abstract).
Dwilinsky, et al., "Excellent Crystallinity of Truly Bulk Ammonothermal GaN," Journal of Crystal Growth 310, pp. 3911-3916, Jun. 18, 2008, doi:10.1016/j.jcrysgro.2008.06.036.
Inoue, T., et al., "Pressure-Controlled Solution Growth of Bulk GaN Crystals under High Pressure," pp. 15-27; Phys. Stat. Sol. (b) 223, 15 (2001).
Iwahashi, et al., "Effects of Ammonia Gas on Threshold Pressure and Seed Growth for Bulk GaN Single Crystals by Na Flux Method," Journal of Crystal Growth, pp. 1-5, 253, Jan. 17, 2003; Elsevier, www.elsevier.com/locate/jcrysgro.
Porowski. S., "Near Defect Free GaN Substrates," MRS Internet Journal of Nitride Semiconductors, Res. 4S1, 1999, G1.3.
Sumiya, et al., "Growth Mode and Surface Morphology of a GaN Film Deposited Along the N-face Polar Direction on c-plane Sapphire Substrate," Journal of Applied Physics, vol. 88, No. 2, pp. 1158-1165, Jul. 15, 2000.
Takahashi, et al., "G-GIXD Characterization of GaN Grown by Laser MBE," The Institution of Electrical Engineers, Stevenage GB, Journal of Crystal Growth Elsevier Netherlands, vol. 237-239, No. 2, pp. 1158-1162, Apr. 1, 2002, XP-002697401, ISSN: 0022-0248.
Wang, B. et al., Inversion Domains and Parallel Growth in Ammonothermally Grown GaN Crystals; Journal of Crystal Growth, Elsevier, Amsterdam, NL. vol. 312, No. 18, Sep. 1, 2010, pp. 2507-2513, XP027184338, ISSN:0022-0248 [retrieved on Apr. 9, 2010] p. 2509, colunm 1, line 16-line 19.
U.S. Appl. No. 13/835,636 Office Action dated Jun. 6, 2014.
U.S. Appl. No. 13/834,871 Office Action dated Jul. 3, 2014.
U.S. Appl. No. 13/835,636 Response dated Sep. 8, 2014.
U.S. Appl. No. 13/835,636 Notice of Allowance dated Sep. 25, 2014.
U.S. Appl. No. 13/834,871 Response dated Oct. 2, 2014.
U.S. Appl. No. 13/834,871 Final Office Action dated Dec. 3, 2014.
U.S. Appl. No. 13/798,530 Non-Final Office Action dated Dec. 26, 2014.
U.S. Appl. No. 13/834,871 Response dated Mar. 3, 2015.
U.S. Appl. No. 13/798,530 Response dated Mar. 26, 2015.
U.S. Appl. No. 13/833,443 Non-Final Office Action dated Apr. 7, 2015.
U.S. Appl. No. 13/834,015 Non-Final Office Action dated Apr. 8, 2015.
U.S. Appl. No. 13/798,530 Final Office Action dated Apr. 22, 2015.
U.S. Appl. No. 13/834,871 Non-Final Office Action dated Jun. 9, 2015.
U.S. Appl. No. 13/833,443 Response dated Aug. 7, 2015.
U.S. Appl. No. 13/834,015 Response dated Aug. 10, 2015.
U.S. Appl. No. 13/833,443 Final Office Action dated Oct. 8, 2015.
U.S. Appl. No. 13/834,015 Notice of Allowance dated Oct. 8, 2015.
U.S. Appl. No. 13/834,871 Response dated Oct. 9, 2015.
U.S. Appl. No. 13/834,871 Final Office Action dated Dec. 16, 2015.
U.S. Appl. No. 13/833,443 Response dated Feb. 8, 2016.
U.S. Appl. No. 13/834,871 Response dated Mar. 16, 2016.
EP 13712085.3 Response and amendment dated Nov. 19, 2015.
EP 13714781.5 Response and amendment dated Nov. 26, 2015.
CN 201380048864.4 Office Action dated Feb. 19, 2016.
U.S. Appl. No. 13/833,443 Notice of Allowance dated Aug. 8, 2016.
EP 13712085.3 Office Action dated Nov. 15, 2017.
U.S. Appl. No. 14/806,632 Notice of Allowability dated Mar. 26, 2018.
EP 13712085.3 Response and Amendment dated Mar. 21, 2018.
EP13715053.8 Office Action dated Mar. 22, 2018.
EP 13714781.5 Office Action dated Mar. 26, 2018.
Landre, et al., "Nucleation Mechanism of GaN Nanowires Grown on (111) Si by Molecular Beam Epitaxy", Nanotechnology 20 (2009) 415602, pp. 1-8, doi: 10.1088/0957-4484/20/41/415602.
Xu, et al., "Fabrication of GaN wafers for electronic and optoelectronic devices," Optical Materials, 23, 2003, pp. 1-5, Elsevier Science B.V., doi:10.1016/30925-3467(03)00051-X.
CN 201380055415.2 Chinese Office Action dated Aug. 21, 2017.
U.S. Appl. No. 14/806,632 Office Action dated Sep. 8, 2017.
U.S. Appl. No. 14/806,632 Amendment dated Dec. 8, 2017.
U.S. Appl. No. 14/806,632 Corrected Notice of Allowability dated Apr. 27, 2018.
U.S. Appl. No. 14/918,474 Office Action dated May 3, 2018.
EP 13712085.3 Communication under Rule 71 (3) dated Jun. 25, 2018.

* cited by examiner

GROUP III NITRIDE WAFERS AND FABRICATION METHOD AND TESTING METHOD

CROSS REFERENCE TO RELATED APPLICATIONS

This application is a Divisional of U.S. patent application Ser. No. 13/798,530, filed Mar. 13, 2013, and entitled "GROUP III NITRIDE WAFERS AND FABRICATION METHOD AND TESTING METHOD," which claims the benefit of priority to U.S. Provisional Patent Application No. 61/706,012, filed Sep. 26, 2012, and entitled "GROUP III NITRIDE WAFERS AND FABRICATION METHOD AND TESTING METHOD," the entire contents of each of which are incorporated by reference herein as if put forth in full below.

This application is related to the following U.S. patent applications:

PCT Utility Patent Application Serial No. US2005/024239, filed on Jul. 8, 2005, by Kenji Fujito, Tadao Hashimoto and Shuji Nakamura, entitled "METHOD FOR GROWING GROUP III-NITRIDE CRYSTALS IN SUPERCRITICAL AMMONIA USING AN AUTOCLAVE";

U.S. Utility patent application Ser. No. 11/784,339, filed on Apr. 6, 2007, by Tadao Hashimoto, Makoto Saito, and Shuji Nakamura, entitled "METHOD FOR GROWING LARGE SURFACE AREA GALLIUM NITRIDE CRYSTALS IN SUPERCRITICAL AMMONIA AND LARGE SURFACE AREA GALLIUM NITRIDE CRYSTALS," which application claims the benefit under 35 U.S.C. Section 119(e) of U.S. Provisional Patent Application Ser. No. 60/790,310, filed on Apr. 7, 2006, by Tadao Hashimoto, Makoto Saito, and Shuji Nakamura, entitled "METHOD FOR GROWING LARGE SURFACE AREA GALLIUM NITRIDE CRYSTALS IN SUPERCRITICAL AMMONIA AND LARGE SURFACE AREA GALLIUM NITRIDE CRYSTALS";

U.S. Utility patent application Ser. No. 60/973,662, filed on Sep. 19, 2007, by Tadao Hashimoto and Shuji Nakamura, entitled "GALLIUM NITRIDE BULK CRYSTALS AND THEIR GROWTH METHOD";

U.S. Utility patent application Ser. No. 11/977,661, filed on Oct. 25, 2007, by Tadao Hashimoto, entitled "METHOD FOR GROWING GROUP III-NITRIDE CRYSTALS IN A MIXTURE OF SUPERCRITICAL AMMONIA AND NITROGEN, AND GROUP III-NITRIDE CRYSTALS GROWN THEREBY";

U.S. Utility patent application Ser. No. 61/067,117, filed on Feb. 25, 2008, by Tadao Hashimoto, Edward Letts, Masanori Ikari, entitled "METHOD FOR PRODUCING GROUP III-NITRIDE WAFERS AND GROUP III-NITRIDE WAFERS";

U.S. Utility patent application Ser. No. 61/058,900, filed on Jun. 4, 2008, by Edward Letts, Tadao Hashimoto, Masanori Ikari, entitled "METHODS FOR PRODUCING IMPROVED CRYSTALLINITY GROUP III-NITRIDE CRYSTALS FROM INITIAL GROUP III-NITRIDE SEED BY AMMONOTHERMAL GROWTH";

U.S. Utility patent application Ser. No. 61/058,910, filed on Jun. 4, 2008, by Tadao Hashimoto, Edward Letts, Masanori Ikari, entitled "HIGH-PRESSURE VESSEL FOR GROWING GROUP III NITRIDE CRYSTALS AND METHOD OF GROWING GROUP III NITRIDE CRYSTALS USING HIGH-PRESSURE VESSEL AND GROUP III NITRIDE CRYSTAL";

U.S. Utility patent application Ser. No. 61/131,917, filed on Jun. 12, 2008, by Tadao Hashimoto, Masanori Ikari, Edward Letts, entitled "METHOD FOR TESTING GROUP III-NITRIDE WAFERS AND GROUP III-NITRIDE WAFERS WITH TEST DATA";

which applications are incorporated by reference herein in their entirety as if put forth in full below.

BACKGROUND

Field of the Invention

This invention is related to a group III nitride wafers used to fabricate various devices including optoelectronic and electronic devices such as light emitting diodes, (LEDs), laser diodes (LDs), photo detectors, and transistors.

Description of the Existing Technology (Note: This patent application refers several publications and patents as indicated with numbers within brackets, e.g., [x]. A list of these publications and patents can be found in the section entitled "References.")

Gallium nitride (GaN) and its related group III nitride alloys are the key material for various optoelectronic and electronic devices such as LEDs, LDs, microwave power transistors and solar-blind photo detectors. However, the majority of these devices are grown epitaxially on heterogeneous substrates (or wafers), such as sapphire and silicon carbide since GaN wafers are extremely expensive compared to these heteroepitaxial substrates. The heteroepitaxial growth of group III nitride causes highly defected or even cracked films, which hinder the realization of high-end electronic devices, such as high-power microwave transistors.

To solve all fundamental problems caused by heteroepitaxy, it is indispensable to utilize group III nitride wafers sliced from group III nitride bulk crystals. For the majority of devices, GaN wafers are favorable because it is relatively easy to control the conductivity of the wafer and GaN wafer will provide the smallest lattice/thermal mismatch with most of device layers. However, due to the high melting point and high nitrogen vapor pressure at elevated temperature, it has been difficult to grow bulk GaN crystals. Currently, majority of commercially available GaN wafers are produced by a method called hydride vapor phase epitaxy (HVPE). HVPE is a vapor phase epitaxial film growth, thus difficult to produce bulk-shaped group III nitride crystals. Due to limitation of the crystal thickness, the typical density of line defects (e.g. dislocations) and grain boundaries is at the order of high $10^5$ to low-$10^6$ cm$^{-2}$.

To obtain high-quality group III nitride wafers of which density of dislocations and/or grain boundaries is less than $10^6$ cm$^{-2}$, a new method called ammonothermal growth, which grows group III nitride crystals in supercritical ammonia, has been developed [1-6]. Currently, high-quality GaN wafers having density of dislocations and/or grain boundaries less than $10^6$ cm$^{-2}$ can be obtained by ammonothermal growth. The ammonothermal growth is an analogue of hydrothermal growth of synthetic quartz, thus is capable of growing bulk group III nitride ingot. There are a few other methods to grow bulk crystals of group III nitride [7-10]. One growth method is a flux-method, which uses group III metal and alkali metal flux. This method can also produce bulk shaped crystal of group III nitride. Yet another growth method is physical vapor transport method, which is basically a sublimation growth. Using these techniques, bulk shaped group III nitride crystal can be obtained recently.

Although wafers of group III nitride crystal can be fabricated by simply slicing the ingot of bulk group III nitride crystal, the slicing process causes damaged layer on the surface. Since the group III nitride crystal is extremely hard material, it is rather difficult to remove the damaged layer. Also, checking the surface finishing is difficult.

SUMMARY OF THE INVENTION

The present invention provides a group III nitride wafer which is sliced from a group III nitride ingot. The wafer may, for instance, be polished to remove an amount of damaged surface layer and tested with x-ray diffraction. The x-ray incident beam is irradiated at an angle less than 15 degrees, and diffraction peak intensity is evaluated. The group III nitride wafer which has passed this test has a sufficient surface quality for device fabrication.

The present invention also provides a method of producing a group III nitride wafer by slicing a group III nitride ingot to produce the wafer, polishing at least one surface of the wafer, and testing the surface quality with x-ray diffraction having an incident beam angle less than 15 degree to the surface.

The present invention also provides the test method of the surface quality of group III nitride wafers using x-ray diffraction having an incident beam angle less than 15 degree to the surface.

BRIEF DESCRIPTION OF THE DRAWINGS

Referring now to the drawings in which like reference numbers represent corresponding parts throughout.

In the figure each number represents the followings:
1. A group III nitride wafer,
2. X-ray incident beam,
3. $2a$. Angle between the x-ray incident beam and the wafer,
4. Diffracted x-ray beam,
5. $3a$. Angle between the diffracted x-ray beam and the wafer,
6. 4. A projection line of the x-ray beam on the wafer.

DETAILED DESCRIPTION OF THE INVENTION

In the following description of the preferred embodiment, reference is made to the accompanying drawings which form a part hereof, and in which is shown by way of illustration a specific embodiment in which the invention may be practiced. It is to be understood that other embodiments may be utilized and structural changes may be made without departing from the scope of the present invention.

Figure 1:
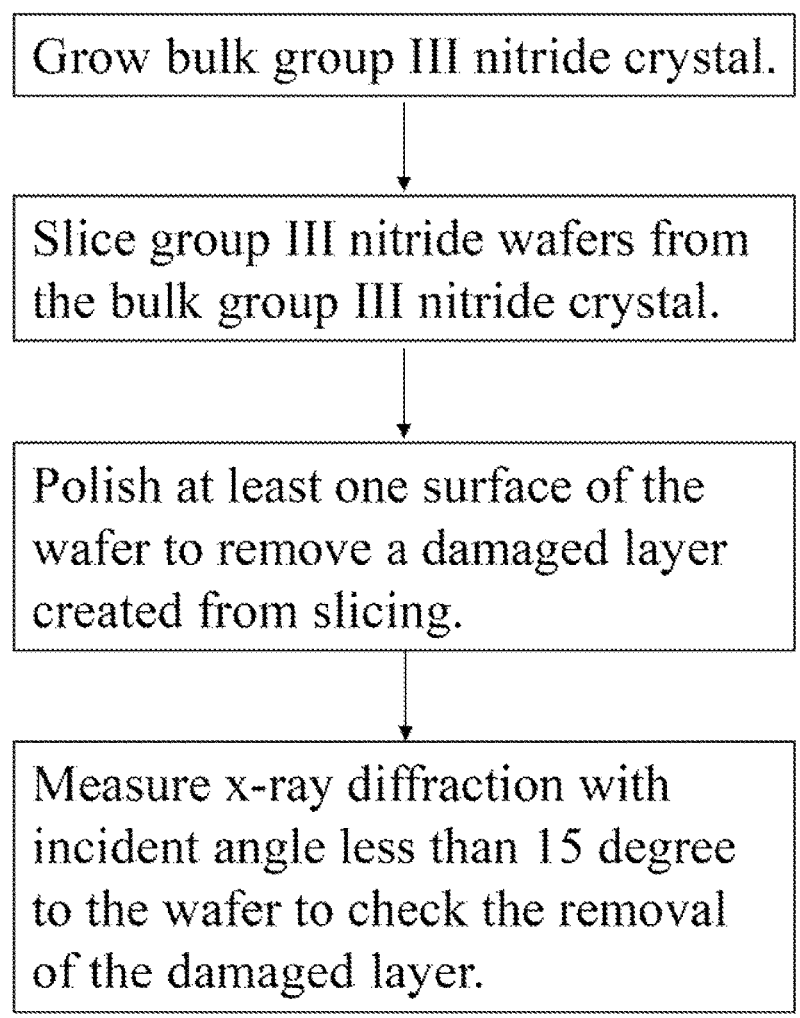
FIG. 1 is an example of process flow of the group III nitride wafer.

Group III nitride wafers such as GaN and AlN are used for optoelectronic and electronic devices, so the surface quality is very important. The group III nitride wafers of the current invention are fabricated with the following steps as shown in FIG. 1. 1) Group III nitride wafers are sliced from a bulk group III nitride crystal. 2) At least one surface of the wafer is polished and a damaged layer introduced during the slicing step is removed. 3) The wafers are tested with x-ray diffraction having an incident beam angle less than 15 degree.

X-ray diffraction is widely used to evaluate crystal quality of materials, but it is typically conducted with a so-called symmetric configuration where the angles of incident beam and diffracted beam are equal. In the case of GaN, for example, 002 diffraction has both incident beam and diffracted beam angles are about 17 degrees to the surface. For 004 diffraction, these angles become about 36 degrees. Because of the high angle of incident beam, the x-ray beam penetrate deeper into the crystal, thus this kind of measurement provides crystal quality of the wafer body.

Figure 2:
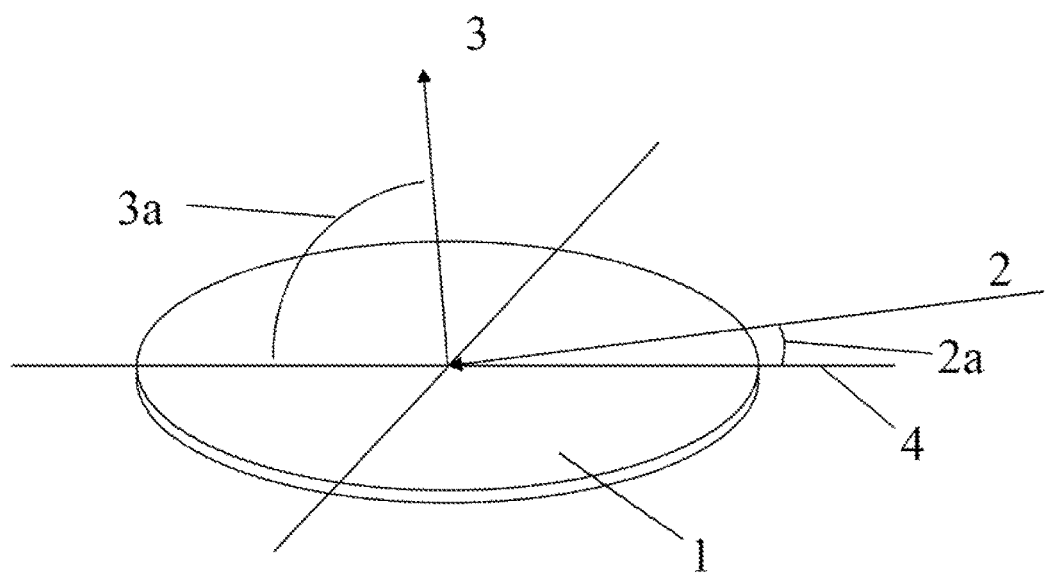
FIG. 2 is an example of x-ray diffraction configuration.

To evaluate the surface damage of the slicing, the angle $2a$ of the incident beam 2 for the x-ray diffraction is set less than 15 degrees as shown FIG. 2. For example, in the case of c-plane GaN, 114 diffraction can be measured by setting the incident beam angle at about 10.9 degrees. In this case, the angle $3a$ of the diffracted beam is about 89.1 degrees. If the surface damage remains on the polished surface of the group III nitride wafer, very weak or no signal from 114 diffraction is detected. By comparing the signal intensity with a diffraction peak from 002, 004, 006, or 008 symmetric measurement or other diffraction peak obtained with an incident angle larger than 15 degrees, the degree of removal of the damaged layer can be evaluated.

The diffraction geometry is often asymmetric, where the angle $3a$ that the diffracted beam 3 makes relative to a line 4 along a face of the wafer is not equal to the angle $2a$ that the incident beam 2 makes with line 4.

Group III nitride wafers which passes the evaluation by this x-ray measurement have a sufficient surface quality for successive device fabrication.

Example 1

An ingot of GaN was grown on a GaN seed crystal with the ammonothermal method using polycrystalline GaN as a nutrient, supercritical ammonia as a solvent, and sodium (4.5 to 5 mol % to ammonia) as a mineralizer. The temperature was between 500 to 550° C. and pressure was between 170 and 240 MPa. The thickness of the bulk GaN crystal was in the range of 3 to 15 mm. By slicing the bulk GaN crystal with a multiple wire saw using steel wire and diamond slurry, we obtained 3 to 20 wafers of GaN. The bulk GaN crystal was sliced along c-plane, thus the sliced wafers were all c-plane oriented.

Then, one of the as-sliced wafers was measured with x-ray diffractometer. First, the incident beam was set to 17.2833 degrees to the Ga surface of the wafer and the detector angle was also set to 17.2833 degrees to the Ga surface of the wafer. Then, 2theta-omega scan showed a 002 diffraction peak with height at approximately 20,000 cps (counts per second). Then the incident beam was set to 10.8662 degrees to the Ga surface of the wafer and the detector angle was set to 89.0886 degrees to the Ga surface of the wafer. The incident beam was irradiated along the 110 direction of the wafer so that 114 diffraction can be detected. In this setting, 2theta-omega scan did not detect any peak from 114 diffraction. Instead of 2theta-omega scan, omega scan can be also used.

The as-sliced wafer was polished with diamond slurry. The wafer was mounted on a metal block with a conventional wax. The Ga-polar surface was facing up so that the Ga-polar surface is polished. Using a rotating polishing machine with a felt pad and 1 micron diamond slurry, the Ga-polar surface of the wafer was polished for a few hours. N-polar surface can be optionally polished if needed. Then, the polished wafer was tested with an x-ray diffractometer. Similar to the as-sliced wafers, x-ray diffraction from 002 and 114 planes were measured. The wafer showed a peak from 002 diffraction with height at approximately 20,000 cps and a peak from 114 diffraction with height approximately 40 cps. The ratio of 114 peak intensity to 002 peak intensity was 1/500. This ratio indicates that there still remains a damaged layer.

After the diamond polishing, the wafer was polished with chemical mechanical polishing (CMP) using colloidal silica having grain size about 10 nm. After a few hours of polishing, the wafer was tested with the x-ray diffractometer and the peak intensities from 002 and 114 diffraction were 20,000 cps and 2300 cps. The peak ratio was 23/200 and removal of the damaged layer was confirmed.

Advantages and Improvements

The current invention provides a group III nitride wafer which is suitable for device fabrication. By testing the polished wafer with x-ray diffraction having an incident beam angle less than 15 degrees to the surface, the quality of the wafer surface is confirmed to be ready for successive device fabrication.

Possible Modifications

Although the preferred embodiment describes GaN crystal, the invention is applicable to other group III nitride alloys, such as AlN, AlGaN, InN, InGaN, or GaAlInN.

Although the preferred embodiment describes ammonothermal growth as a bulk growth method, other growth methods such as high-pressure solution growth, flux growth, hydride vapor phase epitaxy, physical vapor transport, or sublimation growth can be used as long as the growth method can grow a bulk crystal which can be sliced into wafers.

Although the preferred embodiment describes c-plane wafers, the invention is applicable to other orientations such as m-plane, a-plane and semipolar planes including but not limited to 101 plane, 102 plane, 103 plane, 111 plane, 112 plane or 113 plane. Also, the invention is applicable to wafers with misorientation within +/−10 degrees from a low-index planes (such as c-plane, m-plane, a-plane and semipolar planes).

Although the preferred embodiment described Ga-polar surface of c-plane wafers, the invention can be applied to the N-polar surface of any polar or semipolar planes.

Although the preferred embodiment describes slicing with a multiple wire saw, other slicing method such as an inner blade saw, an outer blade saw, multiple blade saw, and a single wire saw can also be used.

Although the preferred embodiment described the 114 diffraction to evaluate the surface damage, diffraction from other crystallographic planes can be used as long as the incident x-ray beam is angled less than 15 degrees to the surface.

Although the preferred embodiment described diamond polishing and CMP using colloidal silica as polishing steps, other polishing steps including gas phase etching can be used.

Consequently, what is disclosed by way of example and not by way of limitation is the following:

1. A wafer of group III nitride crystal sliced from a bulk group III nitride crystal having at least one x-ray diffraction peak for an incident beam at an angle less than 15 degrees to a surface of the wafer.

2. A wafer according to paragraph 1, wherein said surface is a polished surface.

3. A wafer according to paragraph 1 or paragraph 2, wherein said surface is a damaged surface with a sufficient amount of the damaged surface removed that the wafer exhibits said at least one x-ray diffraction peak for an incident beam at an angle less than 15 degrees to the surface.

4. A wafer according to any of paragraphs 1 through 3, wherein the wafer has a surface (a) oriented with c-plane or (b) misoriented from the c plane, and wherein said surface misorientation is within +/−10 degrees.

5. A wafer according to paragraph 4, wherein the diffraction peak is from 114 plane of group III nitride crystal.

6. A wafer according to paragraph 5, wherein peak intensity of the diffraction peak from 114 plane is more than 1/100 of peak intensity of a diffraction peak from 002 plane.

7. A wafer according to any of paragraphs 1 through 3, wherein the wafer is selected from the group consisting of m-, a-, 101, 102, 103, 111, 112 and 113 base-plane wafers, wherein the wafer has a surface (a) oriented with the base-plane or (b) misoriented from the base plane, and wherein said surface misorientation is within +/−10 degrees.

8. A wafer according to any of paragraphs 1 through 7, wherein the group III nitride crystal comprises a gallium nitride crystal.

9. A method of fabricating a wafer of group III nitride comprising (a) growing a bulk crystal of group III nitride, (b) slicing the bulk crystal into wafers, (c) polishing at least one surface of a wafer selected from said wafers until the wafer shows at least one x-ray diffraction peak for an incident beam at an angle less than 15 degrees to the surface.

10. A method according to paragraph 9, wherein the step of polishing comprises polishing using a diamond slurry.

11. A method according to paragraph 9 or paragraph 10, wherein the step of polishing comprises polishing using colloidal silica.

12. A method according to any of paragraphs 9 through 11, wherein the wafer has a surface (a) oriented with c-plane or (b) misoriented from the c plane, and wherein said surface misorientation is within +/−10 degrees.

13. A method according to paragraph 12, wherein the x-ray diffraction is from 114 plane of group III nitride crystal.

14. A method according to paragraph 13, wherein the peak intensity of the diffraction peak from 114 plane is more than 1/100 of the peak intensity of the diffraction peak from 002 plane.

15. A method according to any of paragraphs 9 through 11, wherein the wafer is selected from the group consisting of m-, a-, 101, 102, 103, 111, 112 and 113 base plane oriented wafers, wherein the wafer has a surface (a) oriented with the base-plane or (b) misoriented from the base plane, and wherein said surface misorientation is within +/−10 degrees.

16. A method according to any of paragraphs 9 through 15, wherein the group III nitride comprises gallium nitride.

17. A method of testing surface damage of a wafer of group III nitride sliced from a bulk group III nitride crystal comprising measuring x-ray diffraction peak with an incident beam at an angle less than 15 degrees to the damaged surface.

18. A method according to paragraph 17, wherein the wafer has a surface (a) oriented with c-plane or (b) misoriented from the c plane, and wherein said surface misorientation is within +/−10 degrees.

19. A method according to paragraph 18, wherein the x-ray diffraction peak is from 114 plane of the group III nitride crystal.

20. A method according to paragraph 19, wherein the peak intensity of the diffraction peak from 114 plane is compared with the peak intensity of the diffraction peak from 002 plane.

21. A method according to paragraph 20, and further comprising verifying that the peak intensity of the diffraction peak from 114 plane is more than 1/100 of the peak intensity of the diffraction peak from 002 plane.

22. A method according to any of paragraphs 17 through 21, wherein group III nitride comprises gallium nitride.

REFERENCES

The following references are incorporated by reference herein:

[1] R. Dwiliński, R. Doradziński, J. Garczyński, L. Sierzputowski, Y. Kanbara, U.S. Pat. No. 6,656,615.
[2] R. Dwiliński, R. Doradziński, J. Garczyński, L. Sierzputowski, Y. Kanbara, U.S. Pat. No. 7,132,730.
[3] R. Dwiliński, R. Doradziński, J. Garczyński, L. Sierzputowski, Y. Kanbara, U.S. Pat. No. 7,160,388.
[4] K. Fujito, T. Hashimoto, S. Nakamura, International Patent Application No. PCT/US2005/024239, WO07008198.
[5] T. Hashimoto, M. Saito, S. Nakamura, International Patent Application No. PCT/US2007/008743, WO07117689. See also US20070234946, U.S. application Ser. No. 11/784,339 filed Apr. 6, 2007.
[6] D'Eyelyn, U.S. Pat. No. 7,078,731.
[7]. S. Porowski, MRS Internet Journal of Nitride Semiconductor, Res. 4S1, (1999) G1.3.
[8] T. Inoue, Y. Seki, O. Oda, S. Kurai, Y. Yamada, and T. Taguchi, Phys. Stat. Sol. (b), 223 (2001) p. 15.
[9] M. Aoki, H. Yamane, M. Shimada, S. Sarayama, and F. J. DiSalvo, J. Cryst. Growth 242 (2002) p. 70.
[10] T. Iwahashi, F. Kawamura, M. Morishita, Y. Kai, M. Yoshimura, Y. Mori, and T. Sasaki, J. Cryst Growth 253 (2003) p. 1.

What is claimed is:

1. A method of testing surface damage of a first wafer of group III nitride wafers sliced from a bulk group III nitride crystal comprising measuring an X-ray diffraction peak of the wafer from 114 plane of the group III nitride with an incident beam at an angle less than 15 degrees to the damaged surface.

2. A method according to claim 1, wherein peak intensity of the X-ray diffraction peak with the incident beam at said angle less than 15 degrees to the damaged surface is compared with a peak intensity of a diffraction peak with an incident beam at an angle more than 15 degree to the damaged surface.

3. A method according to claim 1, wherein the wafer has a surface (a) oriented with c-plane or (b) misoriented from the c-plane, and wherein said surface misorientation is within +/−10 degrees.

4. A method according to claim 2, wherein the peak intensity of the diffraction peak from 114 plane is compared with the peak intensity of the diffraction peak from 002 plane.

5. A method according to claim 4, and further comprising verifying that the peak intensity of the diffraction peak from 114 plane is more than 1/100 of the peak intensity of the diffraction peak from 002 plane.

6. A method according to claim 1 wherein the X-ray diffraction peak indicates that the wafer requires removal of the surface damage.

7. A method according to claim 4 wherein the X-ray diffraction peak from 114 plane indicates that the wafer requires removal of the surface damage.

8. A method according to claim 5 wherein the X-ray diffraction peak from 114 plane indicates that the wafer requires removal of the surface damage.

9. A method according to claim 1 wherein the X-ray diffraction peak indicates the degree of removal of the surface damage.

10. A method according to claim 4 wherein the X-ray diffraction peak from 114 plane indicates the degree of removal of the surface damage.

11. A method according to claim 5 wherein the X-ray diffraction peak from 114 plane indicates the degree of removal of the surface damage.

12. A method according to claim 1 wherein the diffraction geometry is asymmetric.

13. A method according to claim 3 wherein the diffraction geometry is asymmetric.

14. A method according to claim 1, wherein group III nitride comprises gallium nitride.

15. A method according to claim 2, wherein group III nitride comprises gallium nitride.

16. A method according to claim 3, wherein group III nitride comprises gallium nitride.

17. A method according to claim 4, wherein group III nitride comprises gallium nitride.

18. A method according to claim 5, wherein group III nitride comprises gallium nitride.

19. A method according to claim 1, wherein the wafer is selected from the group consisting of m-, a-, 101, 102, 103, 111, 112 and 113 base plane oriented wafers, wherein the wafer has a surface (a) oriented with the base-plane or (b) misoriented from the base-plane, and wherein said surface misorientation is within +/−10 degrees.

* * * * *